(12) United States Patent
Shi et al.

(10) Patent No.: US 11,667,541 B2
(45) Date of Patent: Jun. 6, 2023

(54) TWO-DIMENSIONAL (2D) BISMUTH NANOCOMPOSITE, AND PREPARATION METHOD AND USE THEREOF

(71) Applicant: Henan University, Kaifeng (CN)

(72) Inventors: Bingyang Shi, Kaifeng (CN); Jiefei Wang, Kaifeng (CN); Ping Shangguan, Kaifeng (CN); Yong Zhong, Kaifeng (CN); Zhongjie Wang, Kaifeng (CN); Xiaoyu Chen, Kaifeng (CN)

(73) Assignee: HENAN UNIVERSITY, Kaifeng (CN)

( * ) Notice: Subject to any disclaimer, the term of this patent is extended or adjusted under 35 U.S.C. 154(b) by 235 days.

(21) Appl. No.: 17/128,311

(22) Filed: Dec. 21, 2020

(65) Prior Publication Data
US 2021/0198118 A1    Jul. 1, 2021

(30) Foreign Application Priority Data

Dec. 25, 2019   (CN) .......................... 201911359148.3

(51) Int. Cl.
*C01G 29/00* (2006.01)
*C01G 55/00* (2006.01)
*B82Y 30/00* (2011.01)
*B82Y 40/00* (2011.01)

(52) U.S. Cl.
CPC ............. *C01G 29/00* (2013.01); *C01G 55/00* (2013.01); *B82Y 30/00* (2013.01); *B82Y 40/00* (2013.01); *C01P 2004/04* (2013.01); *C01P 2004/24* (2013.01); *C01P 2004/64* (2013.01)

(58) Field of Classification Search
None
See application file for complete search history.

*Primary Examiner* — Jeffrey D Washville
(74) *Attorney, Agent, or Firm* — Shumaker, Loop & Kendrick, LLP; James D. Miller

(57) ABSTRACT

The disclosure relates to a two-dimensional (2D) bismuth nanocomposite, and a preparation method and use thereof, and belongs to the field of nanobiotechnology. The 2D bismuth nanocomposite of the disclosure is an ultra-thin bismuth nanosheet that is loaded with platinum nanoparticles and modified with indocyanine green (ICG) and surface targeting polypeptide Ang-2. The 2D bismuth nanocomposite Bi@Pt/ICG-Ang2 of the disclosure can not only realize the targeted photothermal and photodynamic combination therapy for tumors, but also realize the dual-mode imaging combining CT and fluorescence imaging.

14 Claims, 3 Drawing Sheets

TWO-DIMENSIONAL (2D) BISMUTH NANOCOMPOSITE, AND PREPARATION METHOD AND USE THEREOF

CROSS-REFERENCE TO RELATED APPLICATIONS

This patent application claims priority to Chinese Patent Application No. 201911359148.3 filed on Dec. 25, 2019, the disclosure of which is incorporated herein by reference in its entirety.

FIELD

The disclosure relates to the field of nanobiotechnology, and in particular to a two-dimensional (2D) bismuth nanocomposite, and a preparation method and use thereof.

BACKGROUND

In recent years, China has witnessed aggravated population aging, increasing industrial environmental pollution, and accelerated urbanization. Meanwhile, the prevalence and mortality of tumors among Chinese residents have increased significantly. Malignant tumors have now surpassed cardiovascular diseases (CVD), especially brain tumors, such as glioma. Neurosurgical resection is the main method for treating brain tumors, but invasive surgical treatment will bring huge harm to a patient, and a tumor is likely to relapse after the surgery. Therefore, it is urgent to develop a non-invasive and highly-efficient therapy to achieve efficient treatment of brain tumors. Nanomaterials emerge as a new non-invasive technology for treating brain tumors in recent years. However, due to the presence of the blood-brain barrier (BBB) in brain, the amount of a nanomaterial entering into tumor lesions in brain is greatly reduced, resulting in an unsatisfactory therapeutic effect. Moreover, monotherapy exhibits a low therapeutic efficiency, and cannot meet the treatment needs of people. Researchers have developed a variety of non-invasive combination therapies and a method to introduce a new type of targeted BBB-crossing antibody modification, hoping to improve the accumulation of a nanomaterial in brain tumor lesions and the treatment efficiency of the nanomaterial.

Near-infrared photothermal therapy (PTT) and photodynamic therapy (PDT) are highly-effective non-invasive therapies for tumors. With the rapid development of nanotechnology, various novel nanomaterials provide new ideas and methods for cancer treatment. With the inspire of graphene research, more and more single-layer or multi-layer 2D materials with different physical and chemical properties have been successfully prepared and characterized, such as hexagonal boron nitride (h-BN), black phosphorus (BP), metals and metal oxides, layered double hydroxides (LDHs), transition-metal carbides/carbonitrides (MXenes), and transition-metal dichalcogenides (TMDs). However, these 2D nanomaterials have poor near-infrared light absorption and low material stability, which greatly restricts the use of these nanomaterials in the field of brain tumor treatment.

Ultra-thin bismuth nanosheets are a new type of 2D nanomaterials, which become extremely-potential research materials for bio-phototherapy due to a larger specific surface area (SSA) resulting from a thinner thickness, relatively-high stability, and prominent near-infrared light absorption. However, the low utilization of ultra-thin bismuth nanomaterials for near-infrared light is still a problem that remains to be solved.

SUMMARY

The disclosure is intended to provide a 2D bismuth nanocomposite, and a preparation method and use thereof. The 2D bismuth nanocomposite Bi@Pt/ICG-Ang2 of the disclosure can not only realize the targeted photothermal and photodynamic combination therapy for tumors, but also realize the dual-mode imaging combining computed tomography (CT) and fluorescence imaging.

The disclosure provides a two-dimensional (2D) bismuth nanocomposite, where, the 2D bismuth nanocomposite is an ultra-thin bismuth nanosheet that is loaded with platinum nanoparticles and modified with indocyanine green (ICG) and surface targeting polypeptide Ang-2; and the ultra-thin bismuth nanosheet has a thickness of 1 nm to 5 nm.

Preferably, the ultra-thin bismuth nanosheet has an irregular shape, and a length of 10 nm to 300 nm.

The disclosure further provides a method for preparing the above 2D bismuth nanocomposite, including the following steps:
1) mixing a bismuth powder with an exfoliation solvent, and then grinding a resulting mixture to obtain a bismuth particle solution;
2) subjecting the bismuth particle solution obtained in step 1) to probe ultrasonic exfoliation in an ice bath and then to a first centrifugation, and collecting a resulting supernatant to obtain an ultra-thin bismuth nanosheet solution; subjecting the ultra-thin bismuth nanosheet solution to a second centrifugation, and collecting a resulting precipitate to obtain a bismuth nanosheet; adding water to the bismuth nanosheet to obtain a bismuth nanosheet solution; and subjecting the bismuth nanosheet solution to lyophilization to obtain a bismuth nanosheet powder;
3) placing the bismuth nanosheet powder obtained in step 2) in an atomic deposition device for introducing a platinum precursor and ozone; where, the introduction method includes: 10 cycles of ozone treatment, and 20 to 150 cycles of alternately introducing a platinum precursor and ozone; the cycles are conducted under the following parameters: deposition temperature: −180° C., platinum precursor temperature: −60° C., pulse/exposure/purge time of ozone: 1 s, 10 s, and 20 s respectively, pulse/exposure/purge time of platinum precursor: 0.5 s, 10 s, and 20 s respectively; and the platinum precursor includes trimethyl(methylcyclopentadienyl)platinum;
4) adding water to obtain a Bi@Pt solution, mixing the Bi@Pt solution with an ICG aqueous solution, and stirring a resulting mixture for 10 h to 14 h at 20° C. to 38° C. in the dark; and conducting a third centrifugation, and washing with water to obtain a Bi@Pt/ICG solution; and
5) mixing the Bi@Pt/ICG solution obtained in step 4) with DSPE-PEG-COOH, conducting supersonic treatment, and stirring a resulting mixture for 12 h at 20° C. to 38° C. in the dark; then adding 1-(3-dimethylaminopropyl)-3-ethylcarbodiimide hydrochloride (EDC) and N-hydroxysuccinimide (NHS), successively, and stirring a resulting mixture for 40 min to 50 min; adding the surface targeting polypeptide Ang-2, and stirring a resulting mixture at 20° C. to 38° C. for 12 h for amidation coupling; and conducting a fourth centrifugation, and then washing with water to obtain a Bi@Pt/ICG-Ang2 solution.

Preferably, the first centrifugation is conducted at 1,000 rpm to 3,000 rpm for 5 min; the second centrifugation is conducted at 7,000 rpm to 10,000 rpm for 30 min; the third centrifugation is conducted at 12,000 rpm to 15,000 rpm for 15 min; and the fourth centrifugation is conducted at 12,000 rpm to 15,000 rpm for 15 min.

Preferably, the exfoliation solvent in step 1) includes one of ethanol, i-propanol, N-methyl pyrrolidone and water, or a combination of two or more thereof.

Preferably, in step 2), the probe ultrasonic exfoliation is conducted at 0° C. to 5° C. for 10 h to 15 h, with power of 500 W to 600 W.

Preferably, in step 4), the Bi@Pt solution has a concentration of 1 mg/mL; the ICG aqueous solution has an ICG concentration of 200 μg/mL; and the Bi@Pt solution and the ICG aqueous solution are mixed at a volume ratio of 1:1.

Preferably, in step 5), after the Bi@Pt/ICG solution and DSPE-PEG-COOH are mixed, a final concentration of DSPE-PEG-COOH is 0.1 mg/mL to 2 mg/mL; the DSPE-PEG-COOH and the surface targeting polypeptide Ang-2 have a molar ratio of 1:(1-3); a final concentration of EDC is 0.02 M; and a final concentration of NHS is 0.02 M.

The disclosure further provides use of the above 2D bismuth nanocomposite or a 2D bismuth nanocomposite prepared by the above preparation method in the preparation of drugs targeting tumors.

The disclosure further provides use of the above 2D bismuth nanocomposite or a 2D bismuth nanocomposite prepared by the above preparation method in the preparation of photosensitizers used in photodynamic/photothermal therapy and/or contrast agents used in computed tomography (CT) imaging.

The disclosure provides a 2D bismuth nanocomposite. The 2D bismuth nanocomposite of the disclosure is an ultra-thin bismuth nanosheet that is loaded with platinum nanoparticles and modified with indocyanine green (ICG) and surface targeting polypeptide Ang-2. The surface of the 2D bismuth nanocomposite of the disclosure is loaded with both the ICG photosensitizer and Pt nanoparticles. The introduction of Pt increases the photostability and reduces the photooxidation rate for the ultra-thin bismuth nanosheet. Moreover, the addition of Pt reduces the hypoxic tumor microenvironment and results in the catalysis on hydrogen peroxide in tumors to generate oxygen, thereby increasing the near-infrared PDT efficiency of ICG. Furthermore, the combination of bismuth and ICG can achieve the CT and fluorescence dual-modal imaging for tumors. The 2D bismuth nanocomposite of the disclosure has uniform size, regular appearance, high near-infrared light absorption capacity, excellent brain-targeting performance, and strong dual-modal imaging ability.

DETAILED DESCRIPTION

Figure 1:
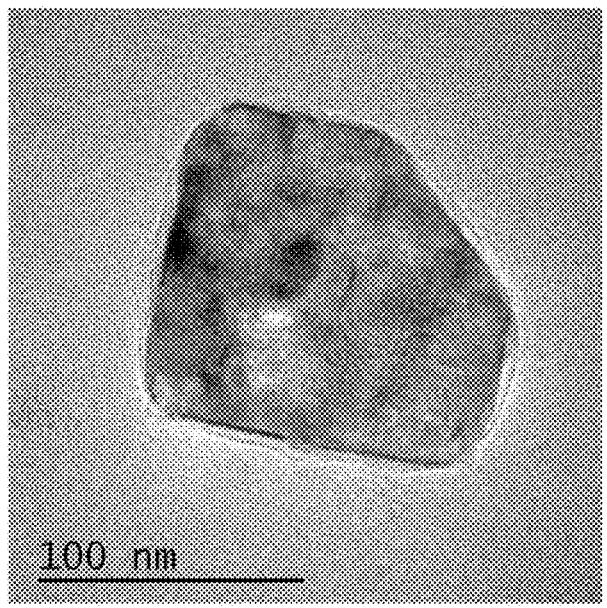
FIG. 1 is a transmission electron microscope (TEM) image of the Bi ultra-thin nanosheet provided by the disclosure.

The disclosure provides a 2D bismuth nanocomposite. The 2D bismuth nanocomposite is an ultra-thin bismuth nanosheet that is loaded with platinum nanoparticles and modified with ICG and surface targeting polypeptide Ang-2; and the ultra-thin bismuth nanosheet has a thickness of 1 nm to 5 nm. The ultra-thin bismuth nanosheet of the disclosure has an irregular shape. In the disclosure, the ultra-thin bismuth nanosheet has a length of 10 nm to 300 nm. The structure of the 2D bismuth nanocomposite of the disclosure includes a 2D material Bi@Pt/ICG (namely, the surface of a 2D bismuth nanocomposite is loaded with both ICG photosensitizer and Pt) and a targeting agent Ang-2 binding to the surface of the 2D material Bi@Pt/ICG. The surface of the 2D bismuth nanocomposite of the disclosure is loaded with both the ICG photosensitizer and Pt nanoparticles. The introduction of Pt increases the photostability and reduces the photooxidation rate for the ultra-thin bismuth nanosheet. Moreover, the addition of Pt reduces the hypoxic tumor microenvironment and results in the catalysis on hydrogen peroxide in tumors to generate oxygen, thereby increasing the near-infrared PDT efficiency of ICG. Furthermore, the combination of bismuth and ICG can achieve the CT and fluorescence dual-modal imaging for tumors.

The disclosure also provides a method for preparing the 2D bismuth nanocomposite in the above technical solution, including the following steps:

1) mixing a bismuth powder with an exfoliation solvent, and then grinding a resulting mixture to obtain a bismuth particle solution;

2) subjecting the bismuth particle solution obtained in step 1) to probe ultrasonic exfoliation in an ice bath and then to a first centrifugation, and collecting a resulting supernatant to obtain an ultra-thin bismuth nanosheet solution; subjecting the ultra-thin bismuth nanosheet solution to a second centrifugation, and collecting a resulting precipitate to obtain a bismuth nanosheet; adding water to the bismuth nanosheet to obtain a bismuth nanosheet solution; and subjecting the bismuth nanosheet solution to lyophilization to obtain a bismuth nanosheet powder;

3) placing the bismuth nanosheet powder obtained in step 2) in an atomic deposition device for introducing ozone and a platinum precursor; where, the introduction method includes: 10 cycles of ozone treatment, and 20 to 150 cycles of alternately introducing ozone/platinum precursor; the cycles are conducted under the following parameters: deposition temperature: −180° C., platinum precursor temperature: −60° C., pulse/exposure/purge time of ozone: 1 s, 10 s, and 20 s respectively, pulse/exposure/purge time of platinum precursor: 0.5 s, 10 s, and 20 s respectively; and the platinum precursor includes trimethyl(methylcyclopentadienyl)platinum;

4) adding water to obtain a Bi@Pt solution, mixing the Bi@Pt solution with an ICG aqueous solution, and stirring a resulting mixture for 10 h to 14 h at 20° C. to 38° C. in the dark; and conducting a third centrifugation, and washing with water to obtain a Bi@Pt/ICG solution; and 5) mixing the Bi@Pt/ICG solution obtained in step 4) with DSPE-PEG-COOH, conducting supersonic treatment, and stirring a resulting mixture for 12 h at 20° C. to 38° C. in the dark; then adding 1-(3-dimethylaminopropyl)-3-ethylcarbodiimide hydrochloride (EDC) and N-hydroxysuccinimide (NHS), successively, and stirring a resulting mixture for 40 min to 50 min; adding the surface targeting polypeptide Ang-2, and stirring a resulting mixture at 20° C. to 38° C. for 12 h for amidation coupling; and conducting a fourth centrifugation, and then washing with water to obtain a Bi@Pt/ICG-Ang2 solution.

In the disclosure, a bismuth powder is mixed with an exfoliation solvent, and a resulting mixture is then ground to obtain a bismuth particle solution. In the disclosure, the bismuth powder is preferably sieved through a 200-mesh sieve before used. In the disclosure, the grinding is conducted preferably for 1 h to 3 h and more preferably for 1 h. The disclosure has no special limitation on a method for the grinding, and a conventional grinding method may be adopted, such as grinding with a ball mill. The bismuth powder after the grinding has a particle size preferably at micrometer scale or larger, and more preferably of 1 μm to 10 μm. In the disclosure, the exfoliation solvent includes one of ethanol, i-propanol, N-methyl pyrrolidone and water, or a combination of two or more thereof. In the disclosure, when the exfoliation solvent includes ethanol and N-methyl pyrrolidone, the ethanol and N-methyl pyrrolidone are mixed preferably at a volume ratio of 1:1. In the disclosure, the bismuth powder and the exfoliation solvent are mixed at a mass-volume ratio preferably of (0.5-100) mg:1 mL, and more preferably of 1 mg:1 mL.

In the disclosure, after a bismuth particle solution is obtained, the bismuth particle solution is subjected to probe ultrasonic exfoliation in an ice bath and then to a first centrifugation, and a resulting supernatant is collected to obtain an ultra-thin bismuth nanosheet solution; the ultra-thin bismuth nanosheet solution is subjected to a second centrifugation, and a resulting precipitate is collected to obtain a bismuth nanosheet; water is added to the bismuth nanosheet to obtain a bismuth nanosheet solution; and the bismuth nanosheet solution is subjected to lyophilization to obtain a bismuth nanosheet powder. In the disclosure, the probe ultrasonic exfoliation is conducted preferably with an exfoliation solvent being added. In the disclosure, the exfoliation solvent preferably includes one of ethanol, i-propanol, N-methyl pyrrolidone and water, or a combination of two or more thereof. In the disclosure, the probe ultrasonic exfoliation is conducted preferably by a cell disrupter, and the disclosure has no special limitation on the model of the cell disrupter. In the disclosure, the probe ultrasonic exfoliation is conducted with power preferably of 500 W to 650 W and more preferably of 540 W; the probe ultrasonic exfoliation is conducted preferably for 10 h to 15 h and more preferably for 12 h; and the probe ultrasonic exfoliation is conducted preferably at 0° C. to 5° C. In the disclosure, the first centrifugation is conducted preferably at 1,000 rpm to 3,000 rpm for 5 min, and more preferably at 2,000 rpm for 5 min, to remove bulk impurities (including bismuth powder not exfoliated); and the second centrifugation is conducted preferably at 7,000 rpm to 10,000 rpm for 30 min, and more preferably at 10,000 rpm for 30 min. In the disclosure, the bismuth nanosheet solution is preferably stored in a refrigerator at 4° C. In the disclosure, the water is added to disperse bismuth nanosheets. In the disclosure, the exfoliation treatment is conducted to obtain a platy 2D bismuth nanosheet. The disclosure has no special limitation on conditions for the lyophilization, and vacuum lyophilization well known to those skilled in the art may be adopted.

In the disclosure, after a bismuth nanosheet powder is obtained, the bismuth nanosheet powder is placed in an atomic deposition device for introducing a platinum precursor and ozone. The introduction method includes: 10 cycles of ozone treatment, and 20 to 100 cycles of alternately introducing a platinum precursor and ozone; the cycles are conducted under the following parameters: deposition temperature: −180° C., platinum precursor temperature: −60° C., pulse/exposure/purge time of ozone: 1 s, 10 s, and 20 s respectively, pulse/exposure/purge time of platinum precursor: 0.5 s, 10 s, and 20 s respectively; and the platinum precursor includes trimethyl(methylcyclopentadienyl)platinum (MeCpPtMe$_3$). In the disclosure, the atomic deposition device is preferably ANGSTROM-DEPIII. In the disclosure, the ozone is preferably provided by an ozone generator. In the disclosure, the platinum precursor and ozone are preferably introduced alternately for 50 cycles. The introduction of Pt increases the photostability and reduces the photooxidation rate for the ultra-thin bismuth nanosheet. Moreover, the addition of Pt reduces the hypoxic tumor microenvironment and results in the catalysis on hydrogen peroxide in tumors to generate oxygen, thereby increasing the near-infrared PDT efficiency of ICG.

In the disclosure, after a Bi@Pt solution is obtained by adding water, the Bi@Pt solution is mixed with an ICG aqueous solution, a resulting mixture is stirred for 10 h to 14 h at 20° C. to 38° C. in the dark, then subjected to a third centrifugation, and washed with water to obtain a Bi@Pt/ICG solution. In the disclosure, the Bi@Pt solution has a concentration preferably of 1 mg/mL; the ICG aqueous solution has an ICG concentration preferably of 200 μg/mL; and the Bi@Pt solution and the ICG aqueous solution are mixed at a volume ratio preferably of 1:1. In the disclosure, the stirring in the dark is conducted preferably at 25° C. for 12 h. In the disclosure, the third centrifugation is conducted at 12,000 rpm to 15,000 rpm for 15 min. In the disclosure, the washing with water is conducted preferably 2 times. In the disclosure, the stirring in the dark is conducted preferably for 12 h. The near-infrared photosensitizer can be introduced to achieve PDT, thereby realizing the photothermal and photodynamic combination therapy.

In the disclosure, after a Bi@Pt/ICG solution is obtained, the Bi@Pt/ICG solution is mixed with DSPE-PEG-COOH, supersonic treatment is conducted, and a resulting mixture is stirred for 12 h at 20° C. to 38° C. in the dark; then EDC and NHS are added successively, and a resulting mixture is stirred for 40 min to 50 min; the surface targeting polypeptide Ang-2 is added, and a resulting mixture is stirred at 20° C. to 38° C. for 12 h for amidation coupling, then subjected to a fourth centrifugation, and then washed with water to obtain a Bi@Pt/ICG-Ang2 solution. In the disclosure, after the Bi@Pt/ICG solution and the DSPE-PEG-COOH are mixed, a final concentration of DSPE-PEG-COOH is preferably 0.1 mg/mL to 2 mg/mL, and more preferably 0.5 mg/mL; and the DSPE-PEG-COOH and the surface targeting polypeptide Ang-2 have a molar ratio preferably of 1:(1-3), and more preferably of 1:1.2. In the disclosure, the ultrasonic treatment is conducted preferably for 10 min to 30 min and more preferably for 20 min, preferably with power of 80 W. In the disclosure, after the ultrasonic treatment, stirring is conducted preferably at 37° C. for 12 h in the dark. In the disclosure, a final concentration of the EDC is preferably 0.02 M, and a final concentration of NHS is preferably 0.02 M. In the disclosure, after EDC and NHS are added, a resulting mixture is preferably stirred for 50 min. In the disclosure, after the surface targeting polypeptide Ang-2 is added, a resulting mixture is preferably stirred at 37° C. for 12 h. In the disclosure, the fourth centrifugation is conducted preferably at 12,000 rpm for 15 min.

The disclosure also provides use of the 2D bismuth nanocomposite according to the above technical solution or a 2D bismuth nanocomposite prepared by the preparation method according the above technical solution in the preparation of drugs targeting tumors.

The disclosure also provides use of the 2D bismuth nanocomposite according to the above technical solution or a 2D bismuth nanocomposite prepared by the preparation method according to the above technical solution in the preparation of photosensitizers used in photodynamic/photothermal therapy and/or contrast agents used in CT imaging.

The 2D bismuth nanocomposite and a preparation method and use thereof according to the disclosure will be further described in detail below with reference to a specific example. The technical solution of the disclosure includes, but is not limited to, the following example.

Example 1

(1) Preliminary physical grinding: A bismuth powder was sieved through a 200-mesh sieve and then mixed with an N-methyl pyrrolidone solvent, and a resulting mixture was ground in a ball mill for 1 h to obtain a bismuth particle solution, where bismuth particles had a smaller particle size (above micrometer scale) and a concentration of 50 mg/mL.

(2) Secondary liquid-phase exfoliation: 1.6 mL of the above preliminarily-ground bismuth particle solution was taken and then placed in a cell disrupter, and probe ultrasonic exfoliation (power: 500 W) was conducted for 15 h in ice water. Then a resulting solution was centrifuged at a low speed (2,000 rpm, 5 min) to remove bulk impurities, and a resulting supernatant (namely, an ultra-thin bismuth nanosheet solution, was collected) and then centrifuged again at a high speed (7,000 rpm, 30 min); a precipitate at the bottom was collected, which was a bismuth nanosheet with a mass of 5 mg to 10 mg, and then 5 mL of water was added for dispersion; and a resulting dispersion was stored in a refrigerator at 4° C. for later use.

(3) The obtained bismuth nanosheet solution was lyophilized, and then a resulting bismuth nanosheet powder was placed in an atomic deposition device (ANGSTROM-DEPIII); and ozone and a platinum precursor (trimethyl(methylcyclopentadienyl)platinum ($MeCpPtMe_3$)) were introduced cyclically through an ozone generator. Ozone treatment was first conducted for 10 cycles, and then ozone and a Pt precursor were introduced alternately for 50 cycles. The cycles were conducted under the following parameters: deposition temperature: −180° C.; precursor temperature: −60° C.; pulse/exposure/purge time of ozone: 1 s, 10 s, and 20 s respectively; pulse/exposure/purge time of platinum precursor: 0.5 s, 10 s, and 20 s respectively.

(4) Adsorption with an ICG photosensitizer: 2 mL of water was added for dispersion to obtain a Bi@Pt solution, and then 200 μg of an ICG solution was added to 1 mL of the above Bi@Pt solution (1 mg/mL); and a resulting mixture was stirred at 20° C. for 12 h in the dark, then centrifuged at 12,000 rpm for 15 min, and washed twice with water to obtain a Bi@Pt/ICG solution.

(5) Ang2 surface modification: 2 mg of DSPE-PEG-COOH was added to 1 mL of the above Bi@Pt/ICG complex solution (1 mg/mL), and a resulting mixture was subjected to ultrasonic treatment for 20 min and then stirred for 12 h at 30° C. in the dark. Then EDC (0.02 M) and NHS (0.02 M) were added successively, and a resulting mixture was stirred for 50 min; and the surface targeting polypeptide Ang-2 was added, and a resulting mixture was stirred at 28° C. for 12 h for amidation coupling, then centrifuged at 12,000 rpm for 15 min, and then washed once with water to obtain a Bi@Pt/ICG-Ang2 solution.

Figure 2:
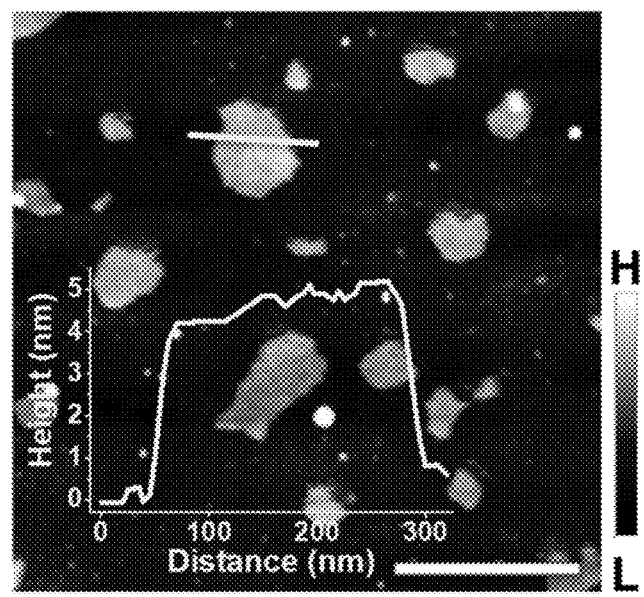
FIG. 2 is an atomic force microscope (AFM) image of the Bi ultra-thin nanosheet provided by the disclosure.
Figure 3:
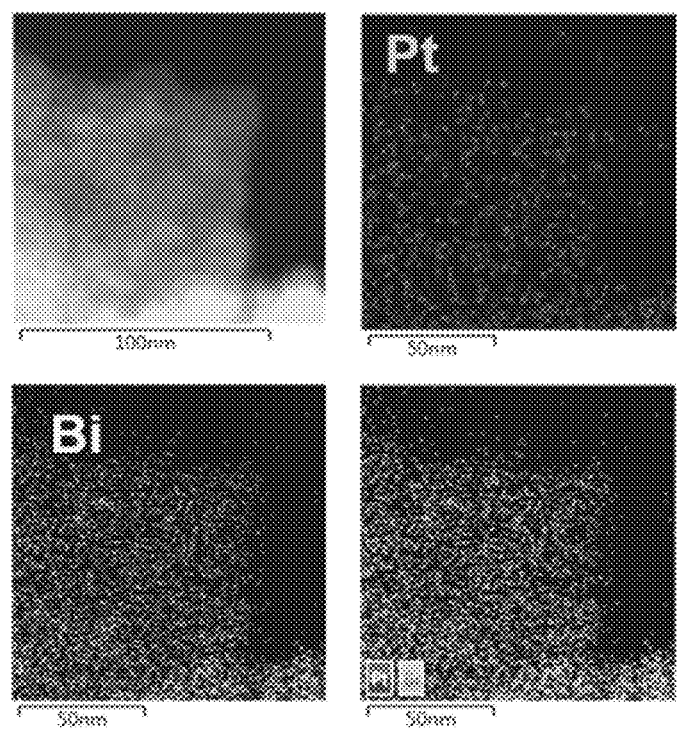
FIG. 3 shows the element mapping images of the Bi@Pt ultra-thin nanosheet provided by the disclosure.

Morphology and size of the 2D bismuth nanocomposite: The 2D bismuth nanocomposite was subjected to TEM and AFM characterization, and results were shown in FIG. 1 and FIG. 2. The results showed that the obtained 2D bismuth nanocomposite had a relatively-regular sheet structure and a thickness of 4 nm. The element mapping results of the obtained Bi@Pt nanomaterial obtained by the ALD method showed that Pt was uniformly deposited on the surface of the bismuth nanosheet (FIG. 3).

Figure 4:
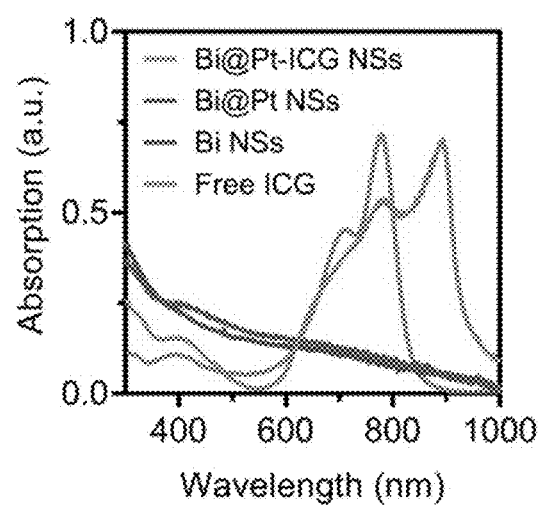
FIG. 4 is a comparison diagram of UV-vis spectra corresponding to the Bi@Pt/ICG ultra-thin nanosheet provided by the disclosure and components thereof.

Combination with the ICG photosensitizer: UV-vis spectrum absorption test was conducted for the Bi@Pt/ICG nanocomposite, and results were shown in FIG. 4. By comparing the absorption spectra of a pure Bi nanosheet, a Bi@Pt nanosheet and a monomer ICG, it could be found that the Bi@Pt/ICG nanocomposite exhibited a clear absorption peak of ICG, indicating that ICG was well adsorbed on the surface of the Bi@Pt nanosheet and an effective combination was achieved. Moreover, the nanocomposite exhibited a high near-infrared absorption capacity at 808 nm, which lays a solid foundation for the subsequent near-infrared photothermal/photodynamic combination therapy.

Figure 5:
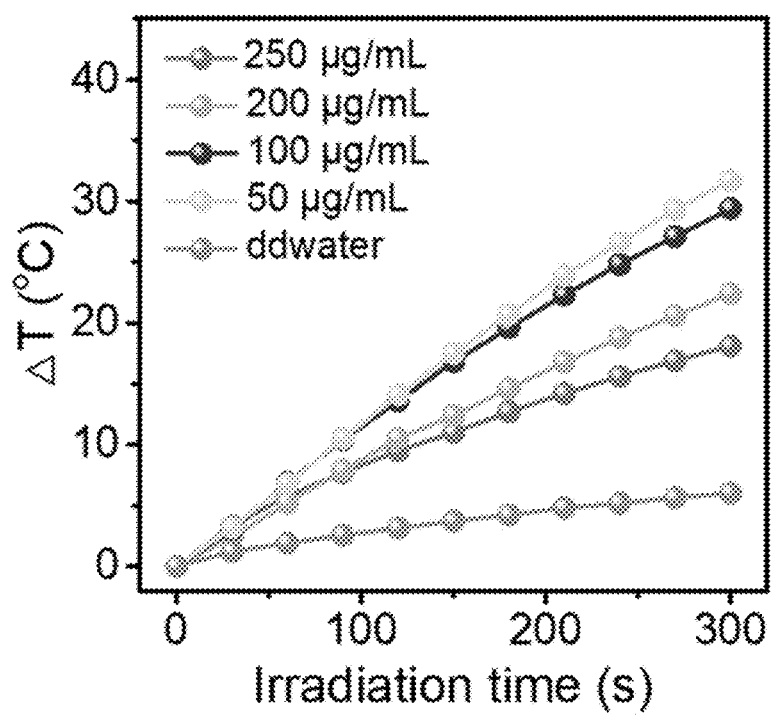
FIG. 5 shows the photothermal efficiency of the Bi@Pt/ICG ultra-thin nanosheet provided by the disclosure at different concentrations.

Photothermal treatment efficiency of the Bi@Pt/ICG nanocomposite: The temperature was monitored for the nanocomposites with different concentrations at 808 nm irradiation, and results were shown in FIG. 5. The results showed that photothermal absorption increased in a significant concentration-dependent manner. It indicated that the Bi@Pt/ICG nanocomposite of the disclosure exhibited a superior photothermal conversion efficiency.

Figure 6:
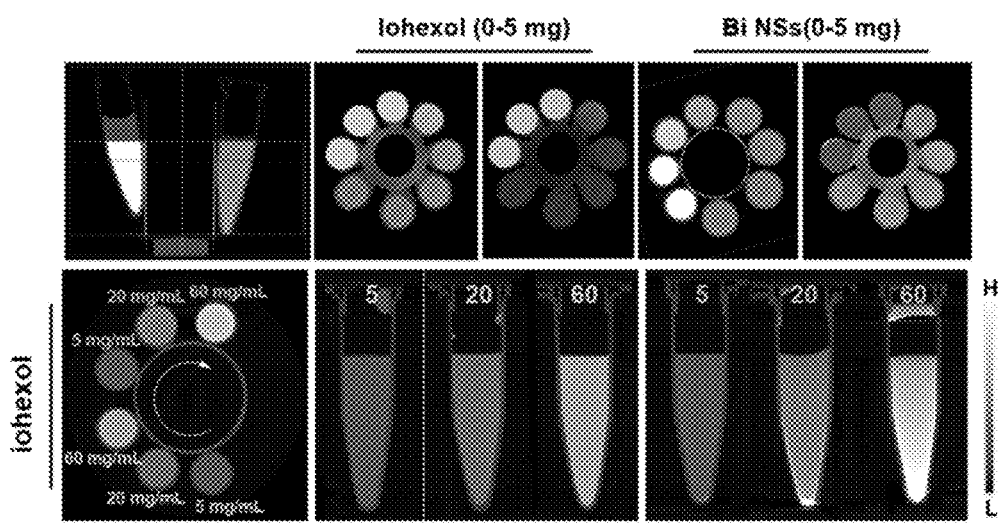
FIG. 6 shows CT images of the Bi ultra-thin nanosheet provided by the disclosure.

CT imaging function of the 2D bismuth nanocomposite: The clinical CT contrast agent of iohexol was used as a control. The CT imaging effects of the two materials at the same concentration were compared, and results were shown in FIG. 6. The results showed that, at the same concentration, the 2D bismuth nanocomposite exhibited a better CT imaging effect due to its Bi atom advantage.

The above descriptions are merely preferred implementations of the disclosure. It should be noted that a person of ordinary skill in the art may further make several improvements and modifications without departing from the principle of the disclosure, but such improvements and modifications should be deemed as falling within the protection scope of the disclosure.

What is claimed is:

1. A two-dimensional (2D) bismuth nanocomposite, the 2D bismuth nanocomposite comprising:
   an ultra-thin bismuth nanosheet that is loaded with platinum nanoparticles and modified with indocyanine green (ICG) and surface targeting polypeptide Ang-2, wherein the ultra-thin bismuth nanosheet has a thickness of 1 nm to 5 nm.

2. The 2D bismuth nanocomposite according to claim 1, wherein, the ultra-thin bismuth nanosheet has an irregular shape, and a length of 10 nm to 300 nm.

3. A method for preparing the 2D bismuth nanocomposite according to claim 1, the method comprising the following steps:
1) Mixing a bismuth powder with an exfoliation solvent, and then grinding a resulting mixture to obtain a bismuth particle solution;
2) Subjecting the bismuth particle solution obtained in step 1) to probe ultrasonic exfoliation in an ice bath and then to a first centrifugation, and collecting a resulting supernatant to obtain an ultra-thin bismuth nanosheet solution; subjecting the ultra-thin bismuth nanosheet solution to a second centrifugation, and collecting a resulting precipitate to obtain a bismuth nanosheet; adding water to the bismuth nanosheet to obtain a bismuth nanosheet solution; and subjecting the bismuth nanosheet solution to lyophilization to obtain a bismuth nanosheet powder;
3) Placing the bismuth nanosheet powder obtained in step 2) in an atomic deposition device for introducing a platinum precursor and ozone; wherein the introduction method comprises: 10 cycles of ozone treatment, and 20 to 150 cycles of alternately introducing a platinum precursor and ozone; the cycles are conducted under the following parameters: deposition temperature: $-180°$ C., platinum precursor temperature: $-60°$ C., pulse/exposure/purge time of ozone: 1 s, 10 s, and 20 s respectively, pulse/exposure/purge time of platinum precursor: 0.5 s, 10 s, and 20 s respectively; and the platinum precursor comprises trimethyl(methylcyclopentadienyl)platinum;
4) Adding water to obtain a Bi@Pt solution, mixing the Bi@Pt solution with an ICG aqueous solution, and stirring a resulting mixture for 10 h to 14 h at 20° C. to 38° C. in the dark; and conducting a third centrifugation, and washing with water to obtain a Bi@Pt/ICG solution; and
5) mixing the Bi@Pt/ICG solution obtained in step 4) with DSPE-PEG-COOH, conducting supersonic treatment, and stirring a resulting mixture for 12 h at 20° C. to 38° C. in the dark; then adding 1-(3-dimethylaminopropyl)-3-ethylcarbodiimide hydrochloride (EDC) and N-hydroxysuccinimide (NHS), successively, and stirring a resulting mixture for 40 min to 50 min; adding the surface targeting polypeptide Ang-2, and stirring a resulting mixture at 20° C. to 38° C. for 12 h for amidation coupling; and conducting a fourth centrifugation, and then washing with water to obtain a Bi@Pt/ICG-Ang2 solution.

4. A method for preparing the 2D bismuth nanocomposite according to claim 2, comprising the following steps:
1) Mixing a bismuth powder with an exfoliation solvent, and then grinding a resulting mixture to obtain a bismuth particle solution;
2) Subjecting the bismuth particle solution obtained in step 1) to probe ultrasonic exfoliation in an ice bath and then to a first centrifugation, and collecting a resulting supernatant to obtain an ultra-thin bismuth nanosheet solution; subjecting the ultra-thin bismuth nanosheet solution to a second centrifugation, and collecting a resulting precipitate to obtain a bismuth nanosheet; adding water to the bismuth nanosheet to obtain a bismuth nanosheet solution; and subjecting the bismuth nanosheet solution to lyophilization to obtain a bismuth nanosheet powder;
3) Placing the bismuth nanosheet powder obtained in step 2) in an atomic deposition device for introducing a platinum precursor and ozone; wherein, the introduction method comprises: 10 cycles of ozone treatment, and 20 to 150 cycles of alternately introducing a platinum precursor and ozone; the cycles are conducted under the following parameters: deposition temperature: $-180°$ C., platinum precursor temperature: $-60°$ C., pulse/exposure/purge time of ozone: 1 s, 10 s, and 20 s respectively, pulse/exposure/purge time of platinum precursor: 0.5 s, 10 s, and 20 s respectively; and the platinum precursor comprises trimethyl(methylcyclopentadienyl)platinum;
4) Adding water to obtain a Bi@Pt solution, mixing the Bi@Pt solution with an ICG aqueous solution, and stirring a resulting mixture for 10 h to 14 h at 20° C. to 38° C. in the dark; and conducting a third centrifugation, and washing with water to obtain a Bi@Pt/ICG solution; and
5) mixing the Bi@Pt/ICG solution obtained in step 4) with DSPE-PEG-COOH, conducting supersonic treatment, and stirring a resulting mixture for 12 h at 20° C. to 38° C. in the dark; then adding 1-(3-dimethylaminopropyl)-3-ethylcarbodiimide hydrochloride (EDC) and N-hydroxysuccinimide (NHS), successively, and stirring a resulting mixture for 40 min to 50 min; adding the surface targeting polypeptide Ang-2, and stirring a resulting mixture at 20° C. to 38° C. for 12 h for amidation coupling; and conducting a fourth centrifugation, and then washing with water to obtain a Bi@Pt/ICG-Ang2 solution.

5. The method according to claim 3, wherein, the first centrifugation is conducted at 1,000 rpm to 3,000 rpm for 5 min; the second centrifugation is conducted at 7,000 rpm to 10,000 rpm for 30 min; the third centrifugation is conducted at 12,000 rpm to 15,000 rpm for 15 min; and the fourth centrifugation is conducted at 12,000 rpm to 15,000 rpm for 15 min.

6. The method according to claim 4, wherein, the first centrifugation is conducted at 1,000 rpm to 3,000 rpm for 5 min; the second centrifugation is conducted at 7,000 rpm to 10,000 rpm for 30 min; the third centrifugation is conducted at 12,000 rpm to 15,000 rpm for 15 min; and the fourth centrifugation is conducted at 12,000 rpm to 15,000 rpm for 15 min.

7. The method according to claim 3, wherein, the exfoliation solvent in step 1) comprises one of ethanol, i-propanol, N-methyl pyrrolidone and water, or a combination of two or more thereof.

8. The method according to claim 4, wherein, the exfoliation solvent in step 1) comprises one of ethanol, i-propanol, N-methyl pyrrolidone and water, or a combination of two or more thereof.

9. The method according to claim 3, wherein, in step 2), the probe ultrasonic exfoliation is conducted at 0° C. to 5° C. for 10 h to 15 h, with power of 500 W to 600 W.

10. The method according to claim 4, wherein, in step 2), the probe ultrasonic exfoliation is conducted at 0° C. to 5° C. for 10 h to 15 h, with power of 500 W to 600 W.

11. The method according to claim 3, wherein, in step 4), the Bi@Pt solution has a concentration of 1 mg/mL; the ICG aqueous solution has an ICG concentration of 200 μg/mL; and the Bi@Pt solution and the ICG aqueous solution are mixed at a volume ratio of 1:1.

12. The method according to claim 4, wherein, in step 4), the Bi@Pt solution has a concentration of 1 mg/mL; the ICG aqueous solution has an ICG concentration of 200 μg/mL; and the Bi@Pt solution and the ICG aqueous solution are mixed at a volume ratio of 1:1.

13. The method according to claim 3, wherein, in step 5), after the Bi@Pt/ICG solution and the DSPE-PEG-COOH are mixed, a final concentration of the DSPE-PEG-COOH is 0.1 mg/mL to 2 mg/mL; the DSPE-PEG-COOH and the surface targeting polypeptide Ang-2 have a molar ratio of 1:(1-3); a final concentration of the EDC is 0.02 M; and a final concentration of the NHS is 0.02 M.

14. The method according to claim 4, wherein, in step 5), after the Bi@Pt/ICG solution and the DSPE-PEG-COOH are mixed, a final concentration of the DSPE-PEG-COOH is 0.1 mg/mL to 2 mg/mL; the DSPE-PEG-COOH and the surface targeting polypeptide Ang-2 have a molar ratio of 1:(1-3); a final concentration of the EDC is 0.02 M; and a final concentration of the NHS is 0.02 M.

* * * * *